US006702747B2

(12) United States Patent  
Garlick

(10) Patent No.: US 6,702,747 B2  
(45) Date of Patent: Mar. 9, 2004

(54) ACOUSTICALLY GENERATED IMAGES HAVING SELECTED COMPONENTS

(75) Inventor: George F. Garlick, Richland, WA (US)

(73) Assignee: Advanced Imaging Technologies, II LLC, Preston, WA (US)

( * ) Notice: Subject to any disclaimer, the term of this patent is extended or adjusted under 35 U.S.C. 154(b) by 0 days.

(21) Appl. No.: 09/982,209

(22) Filed: Oct. 17, 2001

(65) Prior Publication Data

US 2002/0045819 A1 Apr. 18, 2002

Related U.S. Application Data

(63) Continuation-in-part of application No. 09/590,148, filed on Jun. 8, 2000.

(51) Int. Cl.⁷ .................................................. A61B 8/00
(52) U.S. Cl. ...................................................... 600/459
(58) Field of Search ................................ 600/444, 443, 600/442, 432, 455, 438, 454, 457, 459, 437, 447; 73/644

(56) References Cited

U.S. PATENT DOCUMENTS

| 3,564,905 A | 2/1971 | Brenden et al. ............. 73/67.5 |
| 3,742,439 A | 6/1973 | Sheridon ................... 340/5 H |
| 3,879,989 A | 4/1975 | Brenden ................... 73/67.5 H |
| 3,911,729 A | 10/1975 | Collins .................... 73/67.5 H |
| 3,983,529 A | 9/1976 | Langlois ................... 340/5 H |
| 4,028,934 A | 6/1977 | Sollish .................... 73/67.8 S |
| 4,457,175 A | * 7/1984 | Ramsey et al. ............... 73/606 |
| 4,478,481 A | 10/1984 | Fusek et al. ............... 350/3.83 |
| 4,531,410 A | 7/1985 | Crostack .................... 73/603 |
| 4,662,222 A | 5/1987 | Johnson ..................... 73/602 |
| 5,072,722 A | * 12/1991 | Granz ........................ 601/4 |
| 5,179,455 A | 1/1993 | Garlick ...................... 359/9 |
| 5,212,571 A | 5/1993 | Garlick et al. ............... 359/9 |
| 5,235,553 A | 8/1993 | Garlick et al. ............... 367/7 |
| 5,329,202 A | 7/1994 | Garlick et al. ............. 310/334 |
| 5,329,817 A | 7/1994 | Garlick et al. ............... 73/605 |
| 5,740,268 A | 4/1998 | Nishikawa et al. ......... 382/132 |
| 5,796,003 A | 8/1998 | Sandhu et al. ............... 73/603 |
| 5,984,870 A | 11/1999 | Giger et al. ............... 600/443 |
| 5,999,836 A | 12/1999 | Nelson et al. ............. 600/407 |
| 6,032,673 A | 3/2000 | Savage et al. ............. 128/898 |
| 6,176,829 B1 | * 1/2001 | Vilkomerson ............... 600/443 |
| 6,432,053 B1 | * 8/2002 | Fecht et al. ................ 600/437 |
| 6,450,960 B1 | 9/2002 | Rather et al. .............. 600/443 |

* cited by examiner

Primary Examiner—Francis J. Jaworski  
Assistant Examiner—Maulin Patel  
(74) Attorney, Agent, or Firm—SEED IP Law Group PLLC

(57) ABSTRACT

An acoustically generated image includes only selected acoustical components. When an original acoustic signal interacts with an object, the resultant acoustic signal comprises a diffracted component and an undiffracted component. The acoustical images of the present invention are generated with either the diffracted component only or the undiffracted component only. In an alternative embodiment, the acoustically generated image may comprise selected frequency component(s) from the diffracted component of the acoustic signal.

16 Claims, 11 Drawing Sheets

An illustration showing the operation of ultrasonic holography as typically practiced under current art An illustration of inventive improvement of the apparatus incorporating a small acoustically opaque element placed at the focal point of unscattered sound. This results in forming a hologram with scattered sound only which creates a light image on a dark background (i.e. dark background imaging).

An illustration of the apparatus incorporating a planar acoustically opaque element with an opening placed at the position of the focal point of and passing unscattered sound while blocking sound scattered by the object forming a dark image on a light background.

An illustration of inventive improvement of the apparatus incorporating an acoustically planar, opaque element selectively placed to only allow passage of sound scattered at preferential angles from selected volume at the focal plane within the object.

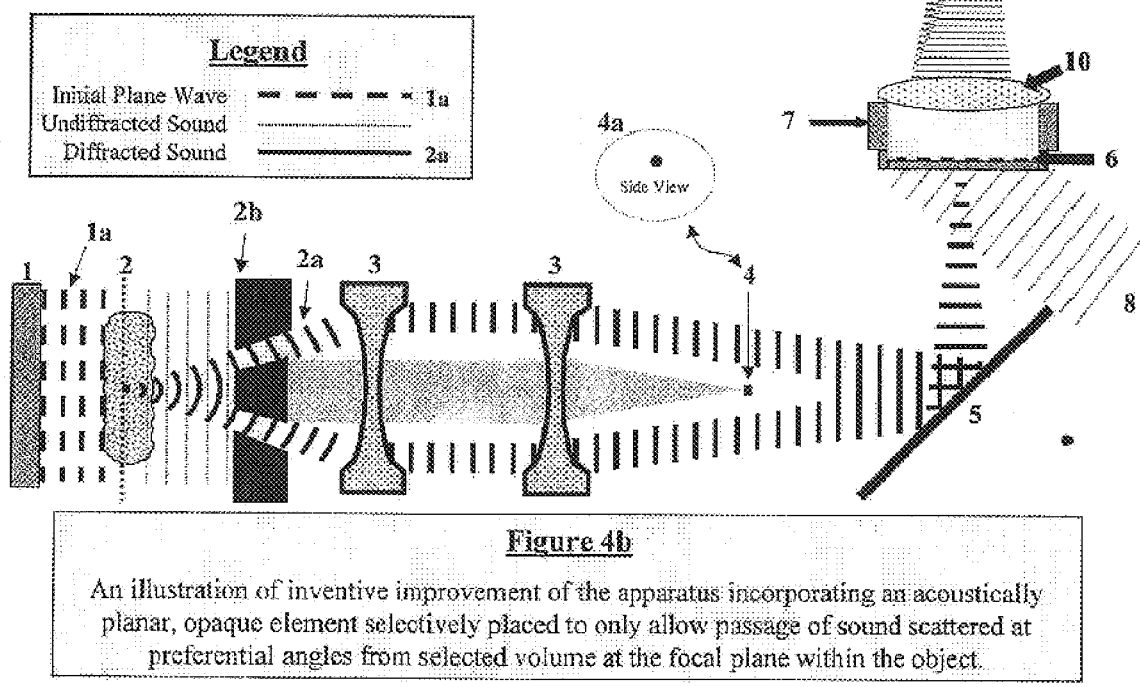

Cross section of acoustically opaque element that minimizes diffraction from the edges Location of position of acoustically opaque element to block unscattered sound wave for multiple off-axis transducer locations

Figure 7a
Primary absorption charateristics of an object results in low scattering angle of image information.

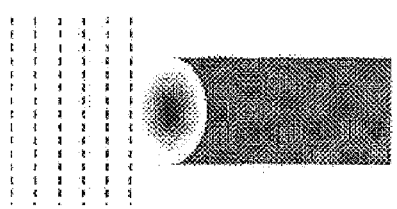

Figure 7b
Abrupt edge charateristics of an object results in medium scattering angle of image information.

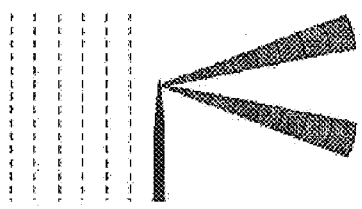

Figure 7c
Point source charateristics of an object results in large scattering angle of image information.

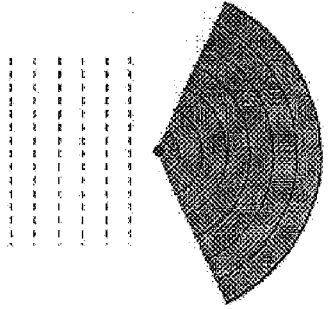

Figure 7
An illustration of how various object charateristics affect forward scattering angle of image information.

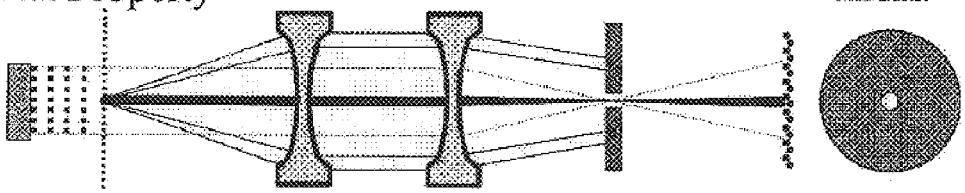
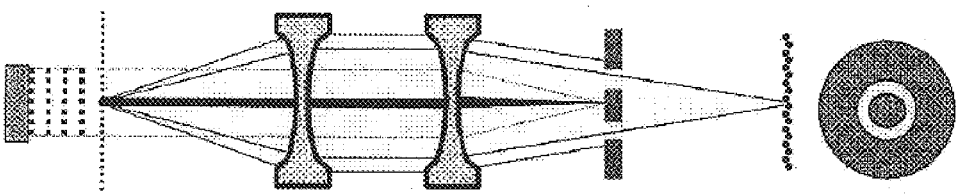
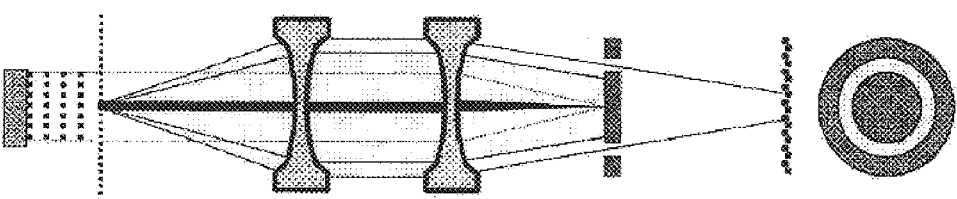
Figure 8
An illustration of imaging with only low (Fig. 8a), medium (Fig. 8b) and high (Fig. 8c) scattering angle information from an object Scattered Sound only Holograms Resolution Targets

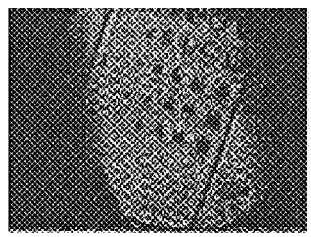

Normal Acoustical Hologram

*Fig. 9A*

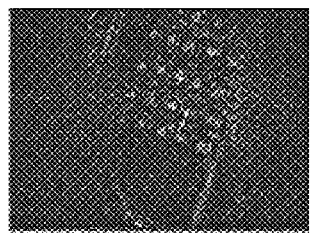

Scattered Sound Only
Acoustical Hologram

*Fig. 9B*

Chicken with fat on the surface

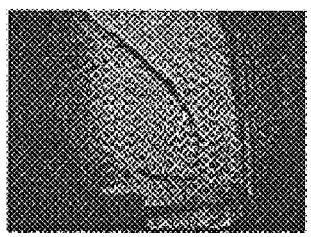

Normal Acoustical Hologram

*Fig. 9C*

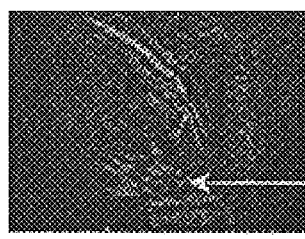

Scattered Sound Only
Acoustical Hologram

*Fig. 9D*

— Notice in scattered sound only imaging, fat tissue is better detected

An exmample of the improved detail of small
and subtle structures from image using only
scattered sound Block position plane for a plane wave source transducer = $L2 - (f_{L2}/((1-(f_{L2}/(L2-L1+f_{L1}))))$ Block position plane for a cylindrical/spherical source transducer = $L2 - ((f_{L2}*O2)/(O2-f_{L2}))$. Where $O2 = L1 \cdot L2 \cdot ((f_{L1}(D+R)/D+R-f_{L1}))$

ACOUSTICALLY GENERATED IMAGES HAVING SELECTED COMPONENTS

CROSS-REFERENCE TO RELATED APPLICATION

This application is a continuation-in-part of U.S. patent application Ser. No. 09/590,148, filed Jun. 8, 2000, now pending, which application is incorporated herein by reference in its entirety.

TECHNICAL FIELD OF THE INVENTION

The present invention is directed generally to acoustic imaging and, more particularly, to an acoustically generated image formed by selected signal components.

The present invention provides a process and an apparatus for enhancing the imaging of subtle structures, such as tumor tissue within a soft tissue matrix. Specifically, the process and apparatus provides a transmissive ultrasonic holography imaging system having an acoustical opaque small element variably placed so as to block the contribution to the image by sound energy transmitted through the object but not scattered by the object being imaged. The present invention further provides a process and apparatus for a transmissive ultrasonic holography imaging system comprising an acoustical opaque planar element having an opening so as to pass unscattered ultrasonic energy (i.e., sound) but to block the contribution to the image by ultrasonic energy that is transmitted through the object and scattered by the object. The present invention further provides an alternate process and apparatus which provides for an acoustical planar element variably placed so as to block all or substantially all of the ultrasonic energy transmitted through the object except that scattered from a selected volume within the object being imaged and at selected forward scattering angles. It is recognized that the nature of the scattering angle relates to the nature of the object being imaged. Thus, in this invention the imaging with selected components refers to imaging with only a selected portion of the ultrasound transmitted through or forward scattered (diffracted) from a structure within an object. The process and apparatus provides for being able to image with only ultrasound scattered at large scattering angles, medium forward scattering angles or low or zero forward scattering angle. Since different characteristics of an object (e.g. lesions in the human breast) forward scatters ultrasonic energy at various angles, by being able to image with ultrasound scattered only selective angles greater and more detailed information can be determined of subtle structures within the object.

The process and apparatus further provides that these two separate image contributions are used and analyzed separately or combined for improved diagnosis of subtle structures. One of the results of utilizing the inventive process provides for improved imaging visualization of subtle objects by providing a means of imaging only with sound scatter from subtle objects because only ultrasound that interferes with the object is transmitted to a holographic detector and reconstructed within the detector. More specifically, the invention provides a process to separately using only specific portions of the transmitted sound wave to make separate images of the object and utilize a combination of such images to provide greater detailed information about subtle structures within the object.

BACKGROUND OF THE INVENTION

Holography involves combining or interfering an object wave or energy with a reference wave or energy to form an interference pattern referred to as the hologram. A fundamental requirement for the forming of the hologram and the practice of holography is that the initial source of the object wave and reference wave or energy are coherent with respect to the other wave. That is to say, that all parts of both the object wave and the reference wave are of the same frequency and of a defined orientation (a fixed spatial position and angle between the direction of propagation of the two sources). When performing holography the object wave is modified by interference with structure within the object of interest. As this object wave interacts with all points of the object in the path of the wave, the three-dimensional features of the object impart identifying phase and amplitude changes on the object wave. Since the reference wave is an unperturbed (pure) coherent wave, its interference with the object wave results in an interference pattern which identifies the 3-D positioning and characteristics (ultrasonic absorption, diffraction, reflection, and refraction) of the scattering points of the object.

A second process, (the reconstruction of the hologram) is then performed when a coherent viewing source (usually light from a laser) is transmitted through or reflected from the hologram. The hologram pattern diffracts light from this coherent viewing or reconstructing source in a manner to faithfully represent the 3-D nature of the object, as seen by the ultrasonic object wave.

To reiterate, to perform holography, coherent wave sources are required. This requirement currently limits practical applications of the practice of holography to the light domain (e.g., a laser light) or the domain of acoustics (sometimes referred to as ultrasound due to the practical application at ultrasonic frequencies) as these two sources are currently the only available coherent energy sources. Thus, further references to holography or imaging system will refer to the through-transmission holographic imaging process that uses acoustical energies usually in the ultrasonic frequency range and more specifically from 1 to 10 MHz.

In the practice of ultrasound holography, one key process is the generation of the ultrasound, such as a large area coherent ultrasound transducer. A second key process is the projection of the object wave information from a specific volume within the object into the hologram detection plane by means of the ultrasonic lens projection system. A third key process is the detection and reconstruction of the ultrasonic hologram into visual or useful format.

Although other configurations can be utilized, a common requirement of the source transducers for both the object and reference waves is to produce a large area plane wave having constant amplitude across the wave front and having a constant frequency for a sufficient number of cycles to establish coherence. Such transducers will produce this desired wave if the amplitude of the ultrasound output decreases in a Gaussian distribution profile as the edge of the large area transducer is approached. This decreasing of amplitude as the edge is approached, reduces or eliminates the "edge effect" from the transducer edge, which would otherwise cause varying amplitude across the wave front as a function distance from the transducer.

In the process of through-transmission ultrasonic holographic imaging, the pulse from the object transducer progresses through the object, then through a focusing lens system and at the appropriate time, the pulse of ultrasound is generated from the reference transducer such that the object wave and reference wave arrive at the detector at the same time to create a interference pattern (i.e., the hologram). For broad applications, the transducers need to be able to operate at a spectrum or bandwidth of discrete frequencies. Multiple frequencies allow comparisons and integration of holograms taken at selected frequencies to provide an improved image of the subtle changes within the object.

A hologram can also be formed by directing the object wave through the object at different angles to the central axis of the lens system. This is provided by either positioning or rotating the object transducer around the central axis of the lens system by using multiple transducers positioned such that the path of transmission of the sound is at an angle with respect to the central axis of the lens system.

With a through-transmission imaging system, it is important to determine the amount of resolution in the "z" dimension that is desirable and achievable. Since the holographic process operates without limits of mechanical or electronic devices to detect and form the image, but rather reconstructs images from wave interactions, the resolution achievable can approach the theoretical limit of ½ the wavelength of the ultrasound used. However, the amount of information displayed for the user in this situation may be too great. It may be desirable to limit the "z" direction image volume so that one can "focus" in on one thin volume slice and thereby reduce the amount of data. Thus, it is of value to develop a means for projecting a planar slice within a volume into the detector plane. One such means is a large aperture ultrasonic lens system that will allow the imaging system to "focus" on a plane within the object. Additionally, this lens system and the corresponding motorized, computer controlled lens drive will allow one to adjust the focal plane and at any given focal plane to be able to magnify or demagnify at a selected z dimension position (i.e., a zoom lens).

The image is detected and reconstructed at the detector. Standard photographic film may be used for the recording of light holograms and the 3-D image reconstructed by passing laser light through the film or reflecting it from the hologram pattern embossed on the surface of an optical reflective surface. However, there is no equivalent "film" material to record the intricate phase and amplitude pattern of a complex ultrasonic wave. One of the most common detectors uses a liquid-air surface or interface to record, in a dynamic way, the ultrasonic hologram formed. The sound energy at the frequency of ultrasound (above range of human hearing) will propagate with little attenuation through a liquid (such as water) but cannot propagate through air. At these higher frequencies (e.g., above 1 MHz) the ultrasound will not propagate through air because the wavelength of the sound energy is so short [$\lambda$(wavelength)=v(velocity)/$f$ (frequency)]. The density of air (approximately 0.00116 g/cm$^3$) is not sufficient to couple these short wavelengths and allow them to propagate. On the other hand the density of a liquid (e.g., water) is a favorable media to couple and propagate such wavelengths. For example, the velocity of sound in air is approximately 346 meters/second whereas in water it is approximately 1497 meter/second. Thus, for water, both the density (1 g/cm$^3$) and the wavelength (~1.5 mm at 1 MHz) are significantly large that ultrasound can propagate with little attenuation. In contrast, for air both the density (0.00116 g/cm$^3$) and wavelength (0.346 mm at 1 MHz) are sufficiently small such that the energy at these ultrasonic frequencies will not propagate.

Thus, when ultrasound propagating in a liquid encounters a liquid-air interface the entire amount of the energy is reflected back into the liquid. Since ultrasound (or sound) propagates as a mechanical force it is apparent that the reflection (or changing direction of propagation) will impart a forward force on this liquid-air interface. This force, in turn, will distort the surface of the liquid. The amount of surface distortion will depend upon the amplitude of the ultrasound wave at each point being reflected and the surface tension of the liquid. Thus, the pattern of the deformation is the pattern of the phase and amplitude of the ultrasonic wave.

In this manner, the liquid-air interface can be readily used to provide a near real-time recorder ("film equivalent") for an ultrasonic hologram. The shape of the surface deformation on this liquid-air detector is the representation of the phase and amplitude of the ultrasonic hologram formed by the interference of the object and reference ultrasonic waves.

The greatest value of the ultrasonic holographic process is achieved by reconstructing the hologram in a usable manner, usually in light, to make visible the structural nature of the initial object. In the case of a liquid-air interface, the reconstruction to achieve the visible image is accomplished by reflecting a coherent light from this liquid-air surface. This is the equivalent process to reflecting laser light from optically generated hologram that is embossed on the surface of a reflecting material (e.g., thin aluminum film).

The reflected light is diffracted (scattered) by the hologram to diffracted orders, each of which contains image information about the object. These diffracted orders are referred to as $\pm n^{th}$ orders. That part of the reconstructing light that does not react with the hologram is referred to as zero order and is usually blocked so that the weaker diffracted orders can be imaged. The higher the diffracted order the greater is the separation angle between the zero order of reflected light. Once reconstructed, the image may be viewed directly, by means of a video camera or through post processing processes.

Ultrasonic holography as typically practiced is illustrated in FIG. 1. A plane wave of sound 1$a$ (i.e., ultrasound) is generated by a large area object transducer 1. Such a transducer is described in U.S. Pat. No. 5,329,202. The sound is scattered (i.e., diffracted) by structural points within the object. The scattered sound 2$a$ from the internal object points that lie in the focal plane 2 are focused (i.e., projected) into a hologram detector plane 6 of a hologram detector 7. The focusing is accomplished by an ultrasonic lens system 3, which focuses the scattered sound into the hologram detector plane 6 and the unscattered sound into a focal point 4. U.S. Pat. No. 5,235,553 describes an ultrasonic lens that may be satisfactorily used for the ultrasonic lenses illustrated as the lens system 3 in FIG. 1. The ultrasonic lens system 3 also allows the imaging process to magnify the image (i.e., zoom) or change focus position. U.S. Pat. No. 5,212,571 illustrates a lens system that can magnify the image and change focus position and may be used satisfactorily for the lens system 3.

Since the focal point 4 of the unscattered sound is prior to the hologram detector plane 6, this portion of the total sound again expands to form the transparent image contribution (that portion of the sound that transmitted through the object as if it were transparent or semi-transparent). In such an application, an ultrasound reflector 5 is generally used to direct the object sound at a different angle, thus impinging on the hologram detector plane 6, which usually contains a liquid that is deformed by the ultrasound reflecting from the liquid-air interface. In an exemplary embodiment, the base of the hologram detector 7 is made to be parallel with the ground so that the thickness of the fluid below hologram plane 6 remains at a constant value.

When a reference wave 8 and the object wave are simultaneously reflected from the hologram detector 7, the deformation of the liquid-air interface is the exact pattern of the ultrasonic hologram formed by the object wave (1a combined with 2a) and the "off-axis" reference wave 8.

This ultrasonic hologram formed on the detector plane 6 is subsequently reconstructed for viewing by using a coherent light source 9, which may be passed through an optical lens 10, and reflected from the holographic detector plane 6. U.S. patent application Ser. No. 09/589,863 describes a hologram detector suitable for use as the hologram detector 7 illustrated in FIG. 1.

This reflected coherent light contains two components. The first component is light that is reflected from the ultrasound hologram that was not diffracted by the ultrasonic holographic pattern, which is focused at position 11 and referred to as undiffracted or zero order light. The second component is light that does get diffracted from/by the ultrasonic hologram is reflected at an "off-axis" angle from the zero order at position 12 and referred to as the "first order" image view when passed through a spatial filter 13. It is noted that this reconstruction method produces multiple diffraction orders each containing the ultrasonic object information. Note also both + and − multiple orders of the diffracted image are present and can be used individually or in combinations to view the optical reconstructed image from the ultrasonically formed hologram by modifying the spatial filter 13 accordingly.

That portion of the ultrasound wave that passes through the imaged object without interference with the object can be a major contributor in "semitransparent objects" (that is, an object that scatters a small portion of the sound waves passed through the object). Since many objects of interest can be rather transparent to sound, (e.g. human soft tissue normal structures and tumor tissue of solid tumors) a major portion of the sound source passes through the object and forms a background hologram that diffracts light to form a bright and strong white light contribution. When one wants to detect and determine the characteristic of subtle changes in the object (e.g., determining tissue characteristics) this background bright image contribution can overpower the resolution of small and subtle contributions of tissue change. Therefore, there is a need in the art to improve resolution characteristics of transmissive ultrasonic imaging so as to be able to distinguish subtle differences within the object (i.e., so as to be able to image tumor tissue within surrounding soft breast tissue).

Furthermore, there is a need in the art to improve image quality by recognizing and utilizing the effects of diffraction generated by internal structures within the object. This need is particularly strong for breast cancer screening techniques that now utilize invasive mammography (providing the patient with exposure to radiation from X-Ray imaging) and yet do not have sufficient sensitivity to certain types of cancerous conditions e.g. cancer not exhibiting calcification or in radiographic dense breasts of young women. The present invention provides this, and other advantages, as will be apparent from the following detailed description and accompanying figures.

SUMMARY OF THE INVENTION

The present invention relates to acoustically generated images of an imaged object. A typical acoustically generated image is generated using one or more of the components resulting from a through transmitted ultrasonic wave forward scattered from the structure within the object being imaged.

The acoustic signal generated by transducers passes through and interacts with an object to produce an acoustic signal having a diffracted component and a nondiffracted component. The acoustic image of the present invention is formed by selected portions of the sound either scattered from or passed through the object being imaged. In use of the present invention, images are generated with either the scattered ultrasound component only, the ultrasound component that is not scattered, a combination thereof or ultrasound forward scattered from structures within the object at a selected angle which may be referred to as at a selected spatial frequency. In one embodiment, the acoustic signals may be ultrasonic acoustic signals. In one embodiment, the acoustically generated image may be a holographic image. The holographic image may be viewed with light (such as a laser light) interaction with the ultrasonic hologram. The holographic image is generated through the interaction of light and an acoustic interference pattern. The acoustic interference pattern may be formed at an liquid-air interface upon which the light is directed.

In an exemplary embodiment, the acoustically generated image information may be constructed by ultrasound that is scattered by internal structures of the object and at a selected angle i.e. at a selected spatial frequency.

BRIEF DESCRIPTION OF THE DRAWINGS

FIG. 4B. illustrates another alternative embodiment of a device used to generate acoustic images only from sound forward scattered at both a selected angle and from a selected position within the object. Note, this configuration will allow the passage and thus image contribution of ultrasound at selected angles such that the scattered sound could only come from a given point within the object.

FIGS. 7A–7C illustrate zero, low and high spatial frequency component, respectively, of forward scattered information from structures within an object.

FIGS. 8A–8C show details of acoustically opaque planar element employed to image with selected components of ultrasound forward scattered from structures within an object.

FIGS. 9A–9D show a series of comparative images of conventional images and the acoustically generated images using selected components of forward scattered ultrasound.

DETAILED DESCRIPTION OF THE INVENTION

The present invention comprises acoustically generated images in which the user has selected which components of the imaging signal passed through an object that will be used to generate the image. Using the apparatus illustrated herein, the user may generate acoustic images having, by way of example, a component diffracted at selected angles only, or the undiffracted component only. As will be described in greater detail below, the acoustic images of the present invention are useful for visualizing an image from selected portions of acoustical energy that passes through the object together with that which does not interfere with the object structure. This allows the image to be constructed from only selected portions of sound or ultrasound or ultrasonic energy that diffracts from, refracts by, or otherwise interferes with (collectively referred to herein as scattered ultrasonic energy) structures within the object. In this manner the inventive acoustically generated images provide an enhancement of subtle structures when compared to the conventional method of imaging with the acoustical holography. As an illustration, it is known that various boundaries or structures of lesions within the human body exhibit different forward scattering angles when illuminated with ultrasonic energy. By utilizing the provisions of this invention and selectively imaging only with forward scattered energy at selected angles, the presence or details of certain edge or structural characteristics may be enhanced. Thus the provisions of this invention will provide additional capability of not only detecting such structures but also the possibility of identifying and characterizing the lesion. Such capabilities will be of great value in the diagnosis and treatment of cancerous tumors versus benign cyst.

Also the ability of this invention to eliminate from the image the undiffracted signal contribution provides a light image on a black background as compared to a black image (the absence of the large diffracted light) as is present in the conventional methods. This method has the additional advantage that the holographic detector is subjected only to a small amplitude (may be less than 10% of the unscattered sound) of image information thus the image signal amplitude to background signal ratio is greatly improved.

Figure 10A:
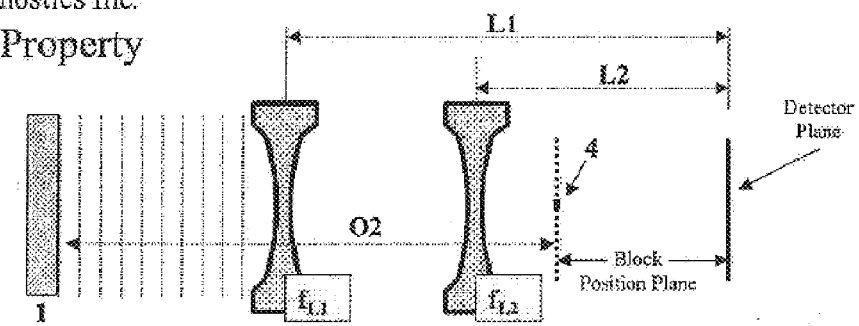
FIGS. 10A–10B illustrate the positioning of acoustically opaque elements to generate the desired acoustic images using different forms of source transducers.
Figure 10B:
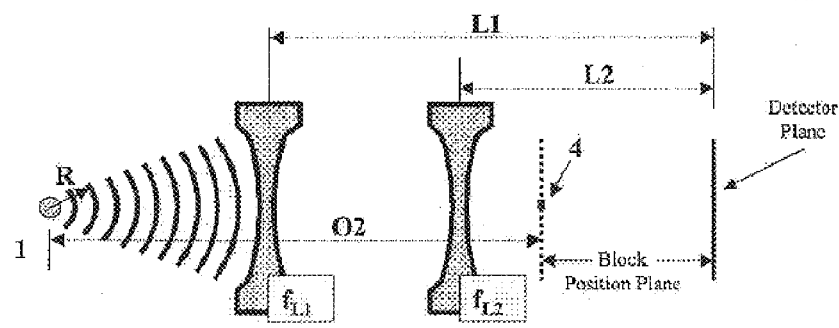

A method and apparatus described herein will track the point and position in which the transmitted unscattered acoustics is to be blocked. Such an apparatus is described in detail in U.S. application Ser. No. 09/590,148, filed on Jun. 8, 2000. This blocking then is positioned by a computer controlled set of driving sources (See FIG. 2) such that the unscattered acoustics is continuously blocked from propagation irrespective of the focus or magnification settings of the lens being used. FIGS. 10a and 10b provide the equations that describe the position for the acoustic signal blocking as a function of lens settings and focal length of the lens.

Figure 1:
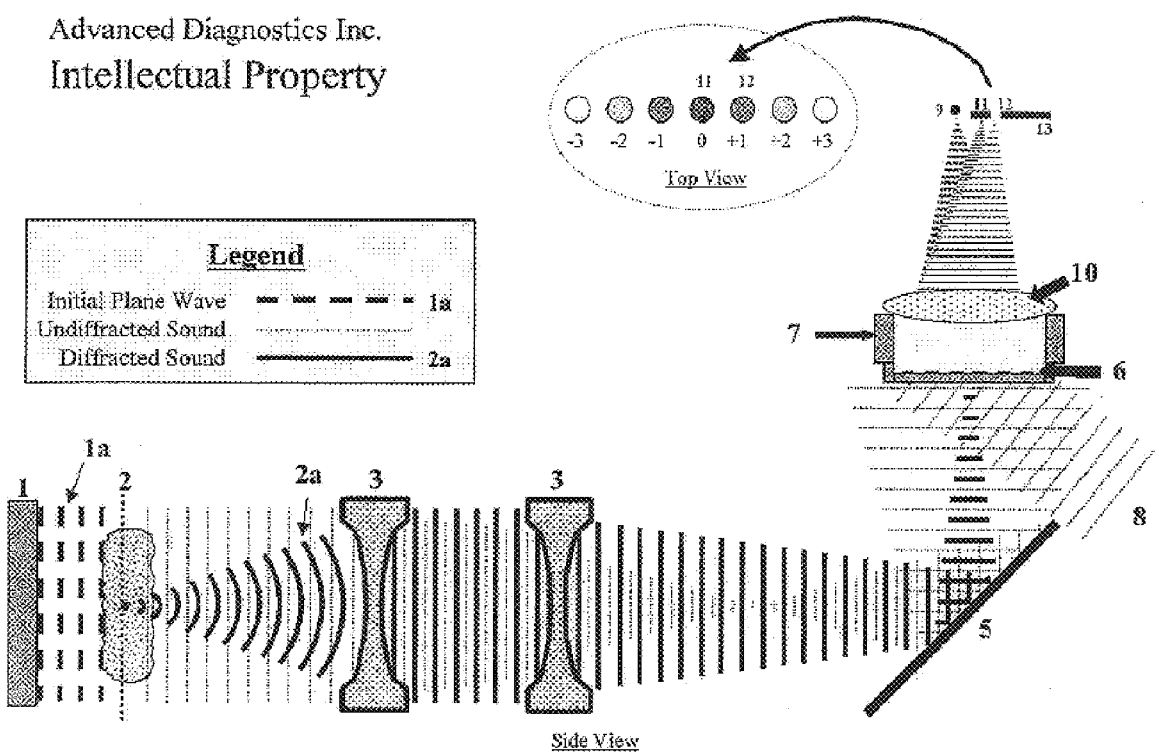
FIG. 1 illustrates conventional apparatus for generating an ultrasonic holographic image.

In the apparatus of FIG. 1, the ultrasonic hologram formed by the object wave includes the diffracted signal component and the undiffracted signal component. The image produced by the apparatus of FIG. 1, if no object is present, is a completely white image. If there is a completely acoustically opaque object, the image will be black. For semi-transparent objects, the inclusion of the non-diffracted signal produces such a strong white background that subtle details of the internal structure of the object are difficult to be seen.

In the operation of the system configuration of FIG. 1, a sound wave, such as a plane wave, is generated from an ultrasonic transducer (i.e., the object source) and is directed at and through the object being imaged. At any point within the object (or any internal structure within the object, such as a tumor mass within breast tissue), the sound wave has the following characteristic interactions:

(1) The object reflects sound waves that do not continue on to the image detector;

(2) The object absorbs sound waves that do not continue on to the image detector;

(3) The object diffracts sound waves and the diffracted waves proceeds on to the image detector; and (4) The object refracts sound waves and the refracted waves proceed on to the image detector.

The inventive acoustical images result from the separation of contributing parts of the ultrasonic wave energy interaction with the structure of the object being imaged. In other words, the acoustically generated image of the present invention may contain only the diffraction portion of an ultrasonic wave interaction with the human body and more specifically only portions that have been scattered at selected angles within the object. Alternatively, the acoustically generated image may contain only undiffracted portion of the ultrasonic wave interaction thus providing information about the absorption and reflection characteristics of the object. In yet another alternative, the acoustic image of the present invention comprises only that portion of the sound that was scattered at selected angles. These separate images yields surprisingly new and detail information about the subtle structures within a object (e.g., cancerous tissue in the human breast). The separation of these various contributing parts of the ultrasound wave interaction with structures within the object being imaged is achieved by specially designed and selectively placed acoustically opaque elements (either small size or planar) to either block or pass portions of the composite ultrasonic wave (i.e., diffraction wave portion).

In the practice of prior art, the various contributions of the ultrasonic wave interaction with the object were all superimposed into one white background image with any structure within the object being indicated as a dark outline within this strong white background image. The net result of the practice of prior art is that the intense white background image overshadows the subtle internal structure detail within the object. Moreover, the edges of internal structures are not as clearly defined as with the new process. This is important as one would like to make accurate measurements of dimensions, such as the exact location and dimension of a tumor lesion within breast tissue.

Figure 2:
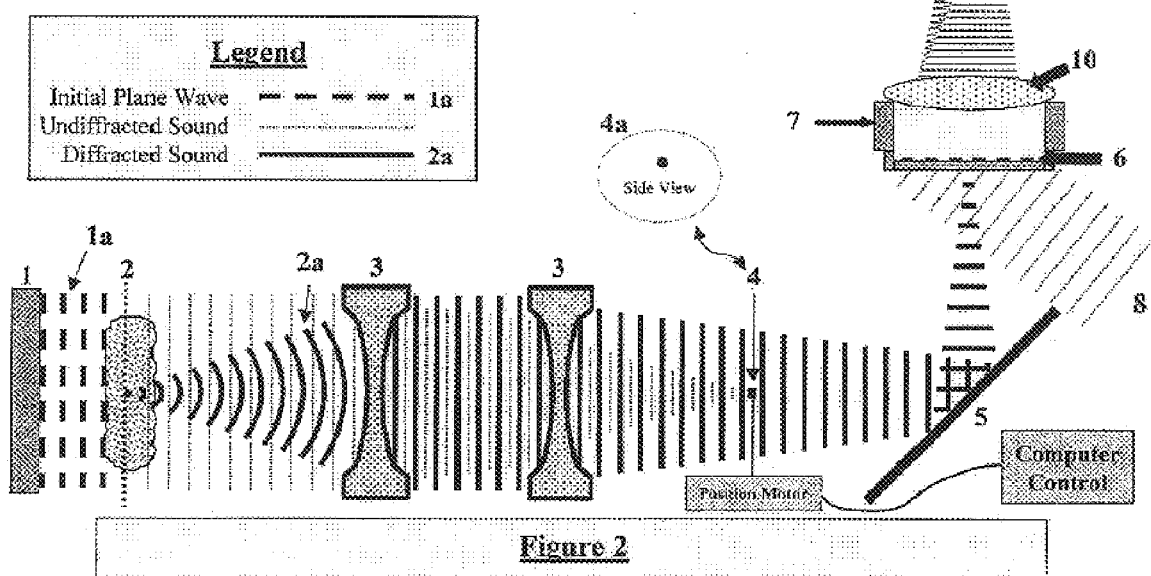
FIG. 2 illustrates an exemplary embodiment of a device used to generate acoustic images of the present invention (note this configuration accepts all scattered ultrasound that is directed such as to pass through the aperture 3a of lens 3 but does not allow image contribution of ultrasound that passes through the object without being scattered and is blocked by 4a).

The addition to the configuration of FIG. 1 adds an acoustically opaque element 4a, shown in FIG. 2, to the acoustic lens system 3 at the focal point 4 of the unscattered sound. In an exemplary embodiment, the planar element 4a is a circular planar element having a diameter less than 1 cm and is positioned at the focal point 4 to prevent transmission of ultrasonic energy directed to the focal point. This improvement results in significant and surprising results to the image quality, including having a black background to aid in imaging lesion dimensions and edges and to better identify internal structures using standard image enhancement techniques. As previously noted, a conventional ultrasonic device produces a strong background, which appears as a white background, making it difficult to discern image details.

With the undiffracted sound blocked by the planar element 4a at the focal point 4 of the unscattered sound, only the diffracted sound resulting from the interference (scattering) with internal structure of the object passes through to the hologram detector plane. The result is a clearer image, but with a white image on a dark or black background in which only the scattered sound information is provided above a zero (i.e., black) background. The black background image contains much more detailed and sensitive information regarding the internal structure of the object that would otherwise be lost in the strong white image of the prior art. It should be noted that the acoustic image generated by the apparatus of FIG. 2 is a completely black image in the absence of any objects within the measured volume. Thus, the subtle internal details are imaged above a black or void background. Such imaging method provides a more sensitive edge and detail imaging as well as showing subtle characteristics of the object.

Figure 3:
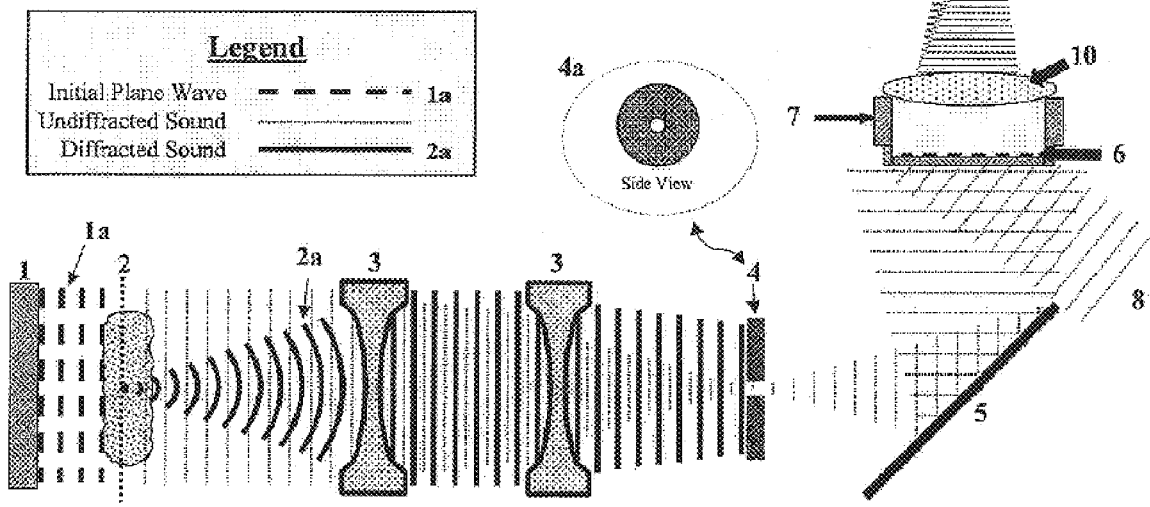
FIG. 3 illustrates an alternative embodiment of a device used to generate acoustic images of the present invention (note, this configuration accepts and utilizes only that ultrasound that passes through the object but is not scattered by that object since all scattered ultrasound is blocked by 4b but all unscattered ultrasound is passed by 4b).

With regard to FIG. 3, an acoustically opaque planar element 4b is placed at the focal point 4 of the unscattered sound. The planar element 4b contains a centrally located aperture through which the focused unscattered sound wave passes. The remainder of the planar element 4b is sized and positioned such that it will block from passage sound that is not directed to this focal point and thus the diffracted or scattered sound is blocked. The acoustically generated image using the apparatus of FIG. 3 has a dark image on a white background, wherein the acoustically generated images using the apparatus of FIG. 2 provides a white image on a black background. Thus, an acoustically generated image having a white background contains information about the absorption and reflection characteristics of the object being imaged and may be compared to the shadow imaging characteristics of a conventional X-Ray. The acoustical image produced by the apparatus of FIG. 3 would be a completely white image in the absence of an object.

The purpose of this novel process and apparatus is to provide a means of seeing only the attenuation and reflection characteristics of the structures of the object being imaged. This is especially important because the X-Ray process, commonly used in medical diagnostics, is a similar process in that the image contrast is formed by recording the amount of radiation that is absorbed within the object (e.g., the human body). Thus, the inventive process for forming the acoustically generated image allows a direct and informative absorption image comparison of X-Ray contrast with that of ultrasound absorption contrast. This comparison is helpful in performing diagnostic imaging such as comparing the image from this new process with that of the standard mammogram image for breast cancer screening imaging.

Figure 4A:
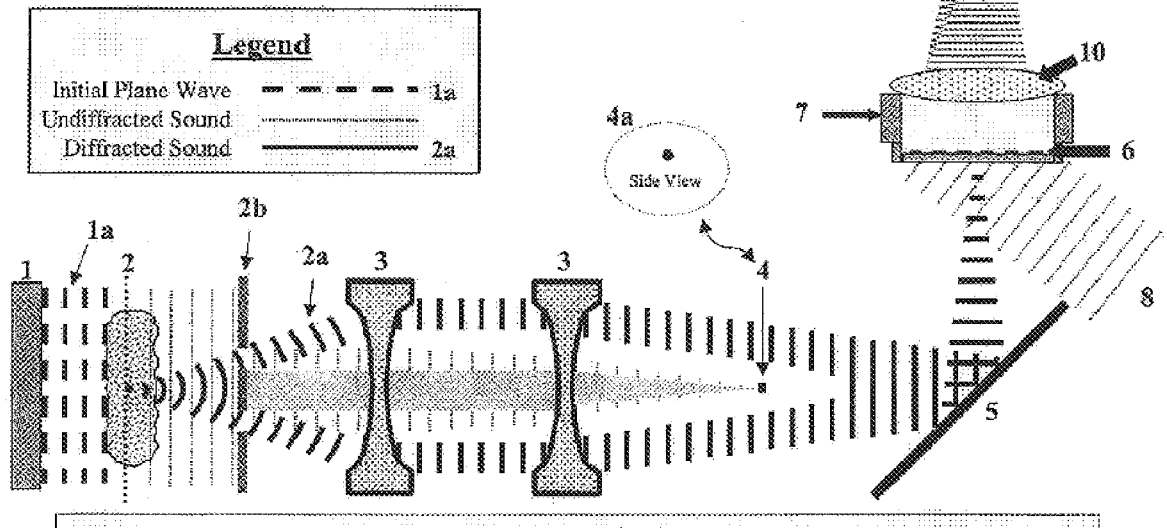
FIG. 4A. illustrates another alternative embodiment of a device used to generate acoustic images only from sound forward scattered at selected angles of the present invention. Note, this configuration allows the passage and thus image contribution of ultrasound a selected angles from scattering points within the object 2 since only the ultrasound scattered at the selected angles will Pass through openings 2a and 2b in ultrasonically opaque element 2c)

In yet another alternative embodiment, illustrated in FIG. 4a, the acoustically generated image results from the forward scattering of image information at selected angles. An acoustically opaque planar element 2a having openings 2b can be placed to selectively allow ultrasonic energy scattered at pre-selected angles for any specified volume within the object to be passed to the detector hologram detector plane 6. Thus, the opaque element 2a may be referred to as a "spatial filter" since it is filtering on the basis of location of an object within the image plane 2. In an exemplary embodiment, the openings 2b of the inner element 2a are positioned symmetrically about the center of the planar element and are selectively positioned between the object and the lens system 3 so as to pass only ultrasonic energy that is scattered at preferential angles from objects positioned within a selected volume in the image plane 2. This will enhance image information from subtle structures within the object being imaged by minimizing or eliminating image contribution from structures outside of a pre-selected volume area within the object.

In addition to increasing sensitivity to subtle details of structures within the object, the illustrated process sharpens the "z" dimension or depth resolution of the imaging process. It should be noted that with the operation of multiple object transducers can be applied to each view to further enhance the sensitivity to a given volume within the object. This process is preferably performed and utilized when the unscattered ultrasonic energy is blocked by acoustically opaque elements, such as the opaque planar element 4a and 4b, shown in FIG. 2 and in FIG. 4, respectively. The acoustically opaque spatial filtering element 2a may alternatively be positioned between the object in the object image plane 2 and the lens system 3, or between the lens system and the hologram detector 7 by repositioning the openings 2b in the opaque planar element to match that of the path of the preferential forward scattering energy.

Figure 5:
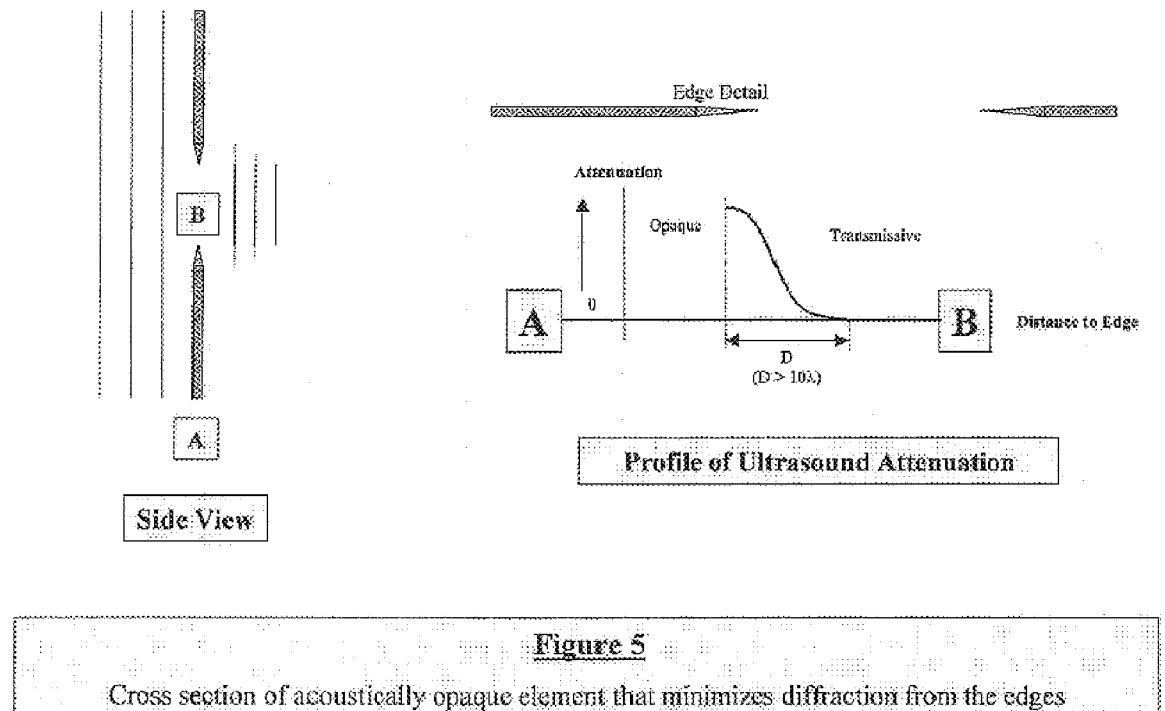
FIG. 5 shows detail of an acoustically opaque planar element exemplary employed in the apparatus of FIGS. 4A–4B (note the edges of all ultrasonically opaque elements have a varying amount of transmissiveness as the edge of the element is approached)

In yet another alternative embodiment, illustrated in FIG. 4b, a device is used to generate acoustic images only from sound forward scattered at both a selected angle and from a selected position within the object. The addition of this configuration is to add the angular restriction of the sound scattered (diffracted) from the object. The result is that this configuration can provide imaging from only a specific volume of interest within an object (e.g. a cancerous condition within the breast). The configuration will allow the detailed examination of a specific volume within the object and at a specified scattering angle. In other words, a selected volume of interest may be imaged at a specific angle of diffraction. This will allow the examination of specific characteristics of the volume of interest since we have established that the scattering (diffraction) angle within an object in indicative of the nature of the object. Thus by allowing ultrasound scattered at selective angles (adjusted by the angle at which sound is allowed to pass through the spatial filter) from a specific volume within the object, one can provide information to determine the subtle nature of the structure in the volume of interest within the object. As those skilled in the art can appreciate, propagating waves are diffracted around sharp edges, such as the opening 2b of the spatial filtering element 2a. If one uses an acoustically opaque spatial filtering element to enhance the diffraction imaging contribution from positions in the focal plane, but then creates additional new diffraction by virtue of the acoustical opaque element itself, it defeats the intended purpose. Thus, it is important to make an improvement to the acoustically opaque element 2a so as to minimize or eliminate diffraction from the element itself. FIG. 5 illustrates a technique to overcome the diffraction of the propagating sound wave from the edge of the acoustically opaque spatial filtering element 2a of FIG. 4. As illustrated in FIG. 5, the edges of the acoustically opaque element 2a are acoustically tapered such that the attenuation starts at or near zero at the edge of the opening 2b and increases over a distance of at least 10 wavelengths of the ultrasonic energy generated by the transducer 1. In this manner, the attenuation of the ultrasound gradually increases as the distance from the opening 2b increases thus minimizing or effectively eliminating diffraction caused by the opening 2b. This design may be applicable to edges of the acoustically opaque element within any sound field, such as the planar elements 4a and 4b, illustrated in FIGS. 2 and 4, respectively.

Figure 6:
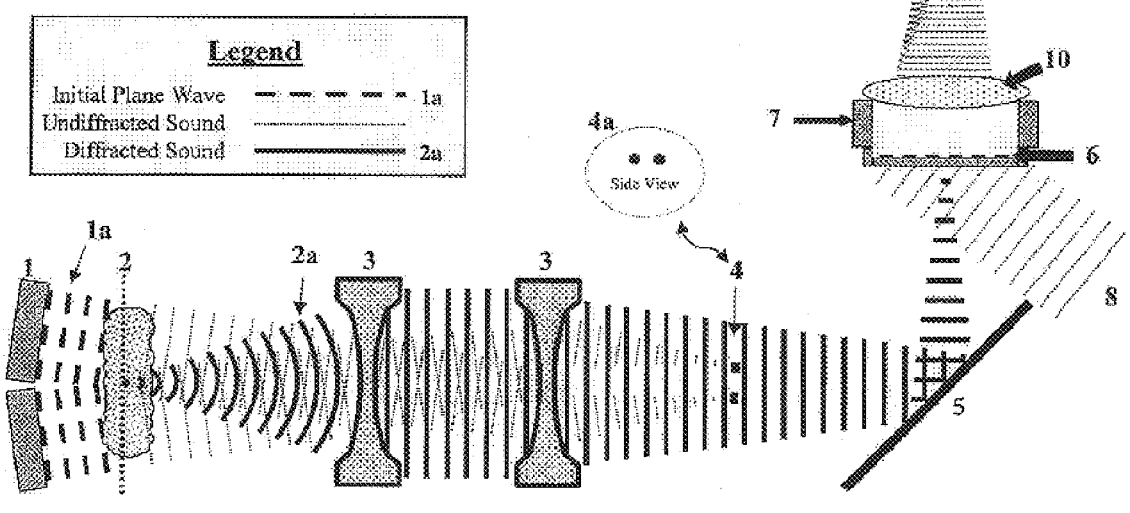
FIG. 6 illustrates yet another alternative embodiment of a device used to generate acoustic images of the present invention (note this configuration illustrates the positioning of two ultrasonically opaque objects to block the unscattered ultrasonic signal from multiple source transducers 1 (blocked by 4a1) and 1a (blocked by 4a2).

Acoustically generated images derived only from the diffraction component may be generated using the apparatus illustrated in FIG. 2. As noted, the object ultrasound wave is generated by a single ultrasound transducer 1. However, it is known in the art to use multiple object ultrasound transducers wherein each of the object transducers is offset from the optical axis of the lens system 3. Such a system is discussed in U.S. Pat. No. 5,329,817. FIG. 6 illustrates an apparatus designed to provide acoustically generated images containing only a diffraction component wherein the object ultrasound signal is generated by multiple offset transducers. The unscattered ultrasonic energy will not be on the center axis of the lens system 3 if the source transducer(s) 1 is or are aligned to propagate sound in a direction that is at an angle (θ) with respect to the central axis of the lens system 3. When the direction of propagation of the unscattered ultrasound signal 1a, is at the angle $\theta_1$ then the acoustical opaque element will be placed at position $4a_1$, which is off-axis from the center line of the lens system 3 and corresponds to the focal point for each of the off-axis transducers. In one embodiment of the inventive apparatus, the source transducers 1 are rotating around the axis of the lens system 3. In this embodiment, the acoustical opaque element is preferably in the shape of a thin strip around the center line of the lens system 3 and encompassing both positions $4a_1$ and $4a_2$.

FIG. 7 illustrates the spatial frequency components present in the ultrasound wave that is forward scattered from a structural component within an object. That is to say when a sound wave interacts with a structure point within an object, the forward scattering can be referred to as having various "spatial frequency". Such designation is consistent with diffraction designation in that the higher the spatial frequency the greater the angle of diffraction. Conversely, the lower the spatial frequency of the scattering, the lower the angle of scattering. Thus, that sound that is only absorbed or reflected can be referred to as zero spatial frequency.

FIG. 8 illustrates the apparatus that is used to image with the selected components described in FIG. 7. Here, an ultrasonic opaque filter with an opening in the center allows the selection of only the zero spatial frequency ultrasound to pass and be imaged (FIG. 7b). By the use of an ultrasonically opaque filter that is opaque in the center and on the peripheral but open between, the image is formed by selectively passing only the low frequency components of the forward scattered wave (FIG. 7c). By blocking all sound propagating at small angles to the center axis but passing all that is at greater angles from the axis, only high spatial frequency components are used in the imaging process (FIG. 7d). Such ability to selective make images with selected components of the forward scattered wave is important in that various structures within an object will have varying characteristics with respect to the scattering frequency. Thus, the use of this invention will allow one to determine the relative amount of low or high spatial frequency components from a given volume. This could lead to characterization of structures within a volume e.g. the differentiation of cancerous structures with the human breast.

FIGS. 9A to 9D show comparative images made with the full ultrasonic energy (white background image) and an acoustically generated image of the present invention in which only the scattered component of the ultrasound signal is contained within the image. As discussed above, the result is a dark background image made with the unscattered ultrasonic energy being blocked from passage to the detector or image plane. In particular, FIG. 9A is a conventional acoustic hologram in which diffracted and undiffracted sound are both directed onto the hologram detector plane 6 (see FIG. 1). FIG. 9B is an acoustic image of the present invention, which contains only the diffracted ultrasonic signal (i.e., scattered from an object within the object plane 2).

FIGS. 9A and 9B are images of a synthetic target designed to illustrate the resolution of acoustic images. In contrast, the acoustic images of FIGS. 9C and 9D are acoustic images of an anatomical component of a chicken. Specifically, FIG. 9C is an image of a chicken with fat on the surface generated by a conventional technology, such as illustrated in FIG. 1. In contrast, the ultrasonic image of the present invention, illustrated in FIG. 9D, is image generated with, by way of example, the apparatus of FIG. 2 or 6, and contains only the diffractive component of the ultrasound signal. It should be noted that the subtle detail of the small holes or the fat content on the piece of chicken meat is not shown in full ultrasonic energy (i.e., the white background) images known in the art, and shown in FIGS. 9A and 9C, but can be seen in the black background diffraction-only acoustic images of the present invention illustrated in FIGS. 9B and 9D. This illustrates improved sensitivity and more detailed information that is possible with the inventive acoustic images.

Regarding FIGS. 10A and 10B, the formulas for the computer control of the positioning of the acoustically opaque element are illustrated for various shape configurations of the initial object of source energy wave. FIGS. 2–4 and 6 illustrate the use of a planar object transducer 1. However, the object wave may be generated from different forms of source transducers, such as spherical or cylindrical object transducers. As can be appreciated by those skilled in the art, the profile of the transducer and the acoustic signal generated thereby affects the position and type of acoustically opaque element used to selectively block portions of acoustic signals. More specifically, FIG. 10A illustrates the object transducer 1 as a planar transducer that generates a planar wave of ultrasonic energy. FIG. 10B illustrates the use of a spherically shaped object transducer 1 and the resultant spherical wave of ultrasonic energy. As previously discussed, and illustrated in FIG. 2, a position motor may be used to properly position the acoustically opaque element. As is known in the art, one or both of the lenses in the lens system 3 may be moved to alter the position of the image plane 2 and/or to alter the magnification of an already selected image plane (i.e., zoom). As the position of the lenses in the lens system 3 are altered, the location of the focal point 4 also moves. The position motor illustrated in FIG. 2 is used to automatically reposition the acoustically opaque element (e.g., the element 4a) so that the acoustically opaque element remains at the desired location (e.g., the focal point 4).

In the illustrated embodiment of FIG. 10A, the planar wave of unscattered ultrasonic energy appears to the lens (L1) to be coming from an infinite distance. Thus, this lens will focus the planar wave unscattered ultrasonic energy to a point from the lens equal to the focal length of the lens (fL1). This same lens means, properly positioned, will focus (in all cases) scattered ultrasonic energy from structures within the object into the plane of a detector, such as the hologram detector 7 illustrated in FIGS. 2–4, 6, and 7. Previous Figures (e.g., FIGS. 1–4) illustrate the hologram detector plane 6 at a different angle from the optical axis. However, for the sake of convenience in illustrating the various focal lengths of lenses in the lens system 3, FIGS. 10A and 10B illustrate the hologram detector plane 6 in alignment with the optical axis of the lenses. If the unscattered ultrasonic energy is not blocked at the focal point 4 unscattered ultrasonic energy (see FIGS. 2 and 6), the unscattered ultrasonic energy proceeds to the holographic detector to form the dominant but less sensitive white image of the object structure in the detector. This prior art imaging process is seen as a darkening from the strong white background resulting from the unscattered ultrasonic energy. As discussed in detail above, blocking the unscattered ultrasonic energy will produce a more sensitive image of subtle details and structures within the object on a black background.

FIG. 10B illustrates the use of a spherically or cylindrical shaped object transducer and a resulting spherical (side view) object sound wave (ultrasonic energy) front. In this case, the unscattered object ultrasonic energy appears to be coming from a point (P) behind the transducer but not from infinity. Thus, this unscattered ultrasonic energy is focused at a position (4s), which is further from the lens means than its focal length, but prior to the hologram detector plane 6. It should be noted that the side view of a cylindrical shaped transducer will respond in the same manner as the spherical shape but in the top view the length of the cylinder will be the length of the acoustically opaque element. Thus, in this embodiment, the acoustically opaque element will be in the shape of a rod whose length is the length of the cylindrical source transducer.

As the magnification of the imaging system is changed, the point at which the undiffracted wave is focused changes. The equations, which describe this position as a function of the magnification (lens position), are shown below.

For Planar Object Wave:
A. For single Acoustic Lens System
   Block Position=L−fL
B. For Double Acoustic Lens System
   Block Position=L2−(fL2/((1−(fL2/(L1−fl1))))
   Where:
      All measurements are from the Hologram Detector Surface
      L is distance to single Acoustic lens
      fL is the focal length of the single lens
      L1, L2 are distances to lens 1 and 2 respectively
      fL1, fL2 are the focal lengths of lens 1 and 2 respectively The Block position and all other measurements are measured from the detector surface A. For Spherical or Cylindrical Object Wave: For a single Acoustic Lens System:
   Block Position=L−fL(R+O)/(R+O−fL)B. For a two Lens System:
   Block Position=L2−((fL2*O2)/(O2−fL2))
   Where: O2=L1−L2−((fL1(D+R)/(D+R−fL1))
      R is the radius of the cylindrical or spherical source transducer
      D is the distance along the center-line of the Lens from L1 to the face of the source transducer
   And: All other measurements are from the Detector Surface
      L is distance to single Acoustic lens
      fL is the focal length of the single lens
      L1, L2 are distances to lens 1 and 2 respectively
      fL1, fL2 are the focal lengths of lens 1 and 2 respectively The Block position and all other measurements are made from the detector surface.

Apparatus

The inventive apparatus provides an improvement to an ultrasonic imaging system using holography for image retrieval and processing. The key elements of the apparatus are an ultrasonic transducer to generate the sound waves directed toward the object to be imaged. One ultrasonic transducer is described in U.S. Pat. No. 5,329,202 ('202 patent), the disclosure of which is incorporated by reference herein. Briefly, FIGS. 4–10 of the '202 patent show an embodiment of an ultrasonic transducer having a thin piezoelectric polycrystalline body or wafer with a large area in parallel between front and back surfaces. The piezoelectric wafer is composed of a polycrystalline ceramic oxide material having piezoelectric activity, such as lead zirconate titanate, which is a known piezoelectric material sometimes identified as PZT. An ultrasonic transducer is designed to generate ultrasonic radiation at a frequency of between 1 MHz and 10 MHz. The piezoelectric wafer has a thickness of approximately 2 mm for a frequency of 1 MHz and approximately 0.7 mm for 3 MHz and 0.2 mm for 10 MHz depending upon the mixture and type piezoelectric material used. Preferably, the thickness is between 1.0 mm and 0.5 mm and most preferably a thickness of 0.8 mm. This transducer will provide a resonant frequency of approximately 2.5 MHz for PZT.

Under one operational mode, the ultrasonic transducer needs to generate large area plane waves necessary to image (on a planar two-dimensional basis) an object as large as a larger woman's breast all the way to the chest wall. Therefore, the ceramic piezoelectric transducer will have a large face surface in the range in size from typically (7.6 cm by 10.16 cm)–77 $cm^2$ to (10.16 cm to 20.32 cm)–309 $cm^2$ in typically a rectangular shape.

The ultrasonic transducer has both a front electrode coating and a back electrode coating applied to the front and back surfaces of the piezoelectric wafer to enable oscillation voltage to be applied to the piezoelectric wafer and to generate a desired large ultrasonic planar wave. Preferably, the electrode coatings completely overlay the respective front and back surfaces of the piezoelectric wafer and have a uniform thickness of approximately 0.0075 to 0.00128 mm. There may be front electrode connector tabs affixed to the front electrode coating for applying a voltage to the front surface, but such tabs may be affixed to a border region so as to avoid interference with the generation of planar waves from the front surface.

There may be a voltage modifying or reduction layer interposed between the back face surface of the piezoelectric crystal and a back electrode coating to reduce the effective voltage applied to the face or front surface of the piezoelectric crystal as the edge of the crystal is approached. This will also minimize the generation of interfering edge effect ultrasonic waves from an edge of the piezoelectric crystal. The voltage reduction layer is composed of a material that is substantially less conductive than the electrode coating material (e.g., synthetic epoxy resin) and provides an electrical impedance between the back electrode and the back surface adjacent to the back edge to reduce the exciting voltage at the side surface to less than 50% (preferably less than 25%) of that applied at the central area of the back side of the piezoelectric crystal. The voltage reduction layer preferably has an electric dielectric constant of between 3 and 100 and an electrical volume resistivity value of between (0.1 ohm-cm and $2.5 \times 10^{15}$ ohm-cm). Most preferably, the voltage reduction layer comprises a synthetic epoxy resin having a dielectric constant between 10 and 20 and an electric volume resistivity of between ($1 \times 10^{15}$ and $5 \times 10^{15}$)ohm-cm.

The ultrasonic transducer provides planar, spherical, or cylindrical sound waves (i.e., ultrasonic energy in the form of waves) propagating in the direction of the object. It is important that the sound waves are transmitted to the object in a medium conducive to propagation of such sound waves. Thus, there is an acoustical path to the object from the transducer to the acoustic lens from the object. Such an acoustical path can be a media with low acoustical attenuation, such as aqueous solutions (e.g., water based or even glycols such as ethylene glycol and glycerol), oil solutions, or rubber pillows making acoustic contact with the object. Preferably, a water bath is provided for breast imaging. In the case of objects that could tend to float in a water bath (not desirable), the object may have to be slightly compressed so that it is better position in the sound path within the water bath.

After passing through the object, the ultrasonic waves are focused to a focal point by the acoustic lens system 3. One such ultrasonic lens system is described in U.S. Pat. No. 5,235,553, the disclosure of which is incorporated by reference herein. Briefly, the individual lenses of the lens system 3 each have a large diameter and is solid, and have an optical axis perpendicular to the periphery and is preferably mounted on a support structure to allow lateral movement along a z-axis (in the direction of propagation of sound waves). Preferably, the solid lens is formed with a homogeneous rigid plastic material that has a transmission velocity with respect to ultrasound (0.5 MHz to 10 MHz) of approximately 1.25 to 2.5 times as great as that of water. The density of the rigid plastic material is preferably between 1.0 and 1.5 that of water. Preferred plastic materials are cross-linked polystyrene or polymethylpentene. Polystyrene has an ultrasonic impedance of approximately 1.8 or less normalized to water (equal 1.0).

The lens preferably has a focal length-to-diameter ratio (f number) of between one and four. Preferably, the focal length "L" is between 20 and 60 cm and the diameter "D" is greater than 15 cm and preferably greater than 20 cm. The lens should also have a diameter-to-thickness ratio of greater than four and preferably between four and twelve. One or both surfaces are formed with multiple radiuses of curvatures so that the incidence ultrasound is focused at the focal plane to provide a focusing of ultrasound waves over the entire face of the lens. The lens is formed such that each small segment or increment of the lens surface has its own radius of curvature so that spherical aberrations are minimized.

An alternative solid ultrasonic lens provides symmetrical solid rigid lens elements, each of which would be classified as a concave-convex lens element. The two lens elements provide a liquid cavity that defines a liquid lens containing a liquid lens material. The solid rigid lens elements each have a convex exterior surface and a concave interior surface. The convex exterior surface and the concave interior surface have different radius of curvatures so that the thickness of each of the elements progressively increases in thickness from the axis to the periphery.

The acoustically opaque element (e.g., the element 4a in FIG. 2) preferentially is able to completely absorb sound. It is an object placed at the focal point of the unscattered ultrasonic energy and has an approximate size of ten fold lambda ($\lambda$) times the $f$ number of the lens means wherein $\lambda$ is the wavelength of the ultrasonic energy used within the media (preferably water). In an exemplary embodiment, the acoustically opaque element is made from an acoustical insulating material having entrapped voids or air. For example, the acoustic insulating material may be selected from the group consisting of cork, porous polymers, open or closed cell foams, and combinations thereof.

Sound then may be directed to an imaging apparatus or reflected to an imaging apparatus using, by way of example, the reflector 5 (see FIG. 2). Preferably, the imaging apparatus uses holography to reconstruct a visual image from the sound waves reaching the imaging apparatus for optical reconstruction. The lens system 3 is positioned, preferably with use of a controller such that the ultrasound energy scattered by structures within the object is focused upon the imaging apparatus. Preferably, the imaging apparatus is an optical hologram reconstruction system utilized in conjunction with a hologram detection surface, preferably a liquid surface that forms an ultrasonic hologram. A coherent light source, such as a laser, generates a coherent light beam that is directed through a collecting lens to illuminate the hologram detection surface. The coherent light illuminating the hologram is reflected from the hologram surface and diffracted into a number of diffraction order beams, and directed to a spatial filter that filters out the undiffracted (zero order) light. All of the diffracted orders contain image information and can be used but preferably, only the first order diffracted beam is allowed to pass to a video camera to be visualized. The video feed can be digitized to pixel signals for a camera. The compilation of pixels that form an image can be averaged over time to minimize or neutralize out-of-focus structures appearing in the images.

Process

The present invention further provides a process for improved imaging of interior structures of an object, comprising:

(a) providing a planar, cylindrical, or spherical sound wave (ultrasonic energy in the form of a wave) to transmit through the object to form a transmitted sound wave having image information resulting from refraction, diffraction, absorption, reflected and the sound that is not scattered by the object (unscattered) sound waves (ultrasonic energy in the form of a wave);

(b) focusing the transmitted and unscattered sound wave to a focal point with an acoustic lens means having a centerline;

(c) providing an acoustically opaque element selectively positioned at the focal point to prevent transmission of ultrasonic energy directed to the focal point; or alternatively an acoustically opaque planar element selectively positioned to pass only that sound that is scattered by structure in the object or alternatively an acoustically opaque planar element selectively positioned to pass only ultrasonic energy scattered from a selected volume within the object being imaged; and (d) imaging the interior structures of the object with a holographic detector having a surface aligned perpendicular to the centerline of the acoustic lens means.

Preferably, in order to demonstrate the comparative advantage of the inventive process having the acoustically opaque element selectively positioned at the focal point of unscattered ultrasonic energy, the foregoing process further comprises (e) repeating the imaging process by placing an acoustical opaque planar element with an opening that allows the passage of the unscattered sound only, the foregoing process further comprises (f) repeating the imaging process by placing and acoustical opaque planar element with circular strip openings that allows passage of only the ultrasonic energy scattered from a selected position in the focal plane of the lens means and (g) comparing characteristics of the object as viewed by the scattered wave imaging with those of the unscattered wave image and finally with the image without blocking any of the transmitted sound to determine greater detailed information of subtle structures of the object being imaged. Preferably, the transmitted sound waves, scattered sound waves, and unscattered sound waves carry spatial phase and amplitude information, on a planar, spherical, or cylindrical basis, corresponding to the three dimensional nature of the object's interior structure. Preferably, the wave generated by the transducer is a planar, cylindrical, or spherical sound wave at a plane perpendicular to the direction of transmission. Most preferably, the acoustic lens system (e.g., the lens system 3) focuses the sound wave to a focal point and any generated diffraction waves generated within the object at the hologram detector surface. Preferably, the transmitted sound wave is focused to the focal point by adjusting the acoustic lens means along a z axis with an electromechanical means. Most preferably, the electromechanical means for adjusting the lens means is controlled by a computer adjusting both the acoustic lens means to form a focal point and positioning the acoustically opaque element at the focal point.

The inventive process allows for improved imaging of internal structures of objects, such as tumor tissue within surrounding breast soft tissue, that utilizes only ultrasound energy that interferes with the structure (tumor tissue). The sound wave that passes through the object carries with it spatial phase and amplitude information about the three dimensional nature of the object's interior structure. In addition, the process provides for an improved and more sensitive visual imaging method that provides white intensity information on a black or void background, when combined with the inventive apparatus having an opaque element placed at the lens focal point. The black background image created provides for improved object identification and size measurements when compared to similar non-reverse (i.e., white) images formed with the same object. Thus, subtle objects or elements within objects can be visualized.

From the foregoing it will be appreciated that, although specific embodiments of the invention have been described herein for purposes of illustration, various modifications may be made without deviating from the spirit and scope of the invention. For example, the inventive acoustic images may be generated by a variety of equipment. Various examples of equipment used to generate the inventive images have been described herein, others may be known in the art. Still other techniques can be derived and applied to create the acoustically generated images of the present invention. Accordingly, the invention is not limited except as by the appended claims.

What is claimed is:

1. An apparatus for generating acoustic images comprising:
   a source of acoustic waves;
   a lens system for receiving the acoustic waves after they have passed through an object; and
   an acoustically opaque element positioned after the lens system for blocking a selected portion of the acoustic wave after it has passed the object and through the lens system.

2. The apparatus according to claim 1 wherein the acoustically opaque member is positioned with an opening at the focal point of the lens and opaque material adjacent the focal point in order to pass unscattered acoustic wave while blocking acoustic waves which have been scattered by the object.

3. The apparatus according to claim 1 wherein the acoustically opaque image is positioned at the focal point to block unscattered acoustic waves and pass acoustic waves which have been scattered by the object.

4. The apparatus according to claim 1 wherein the acoustically opaque member is positioned at a selected location relative to the focal point to allow passage of acoustic waves scattered at peripheral angles from a selected volume within a focal plane of the object.

5. The apparatus according to claim 1 wherein the acoustically opaque member is shaped like a doughnut, having an aperture therein for passing acoustic waves and blocking material in a peripheral region for blocking acoustic waves.

6. The apparatus according to claim 1 wherein the acoustically opaque member is composed of two distinct elements which are positioned to block unscattered acoustic waves at multiple off-axis transducer locations.

7. The apparatus according to claim 1 wherein said acoustically opaque member includes tapered edges adjacent an opening to pass acoustic waves.

8. The apparatus according to claim 1 wherein the acoustically opaque member is a plurality of members, having an outer ring of acoustically opaque material and an inner portion of acoustically opaque material and having an opening to pass acoustic waves between the first and second elements.

9. An apparatus for generating acoustic images comprising:
   a source of acoustic energy;
   a lens system for modifying the acoustic energy after it is passed through an object;
   an imaging system after the lens system, the imaging system being positioned to create an image using information within the acoustic wave after it has passed through an object; and
   an acoustically opaque member positioned between the lens system and the imaging system, the location of the acoustically opaque member being selected to block a certain portion of the acoustic wave and pass another portion of the acoustic wave.

10. The apparatus according to claim 9 wherein the location of the acoustically opaque member is selected based on imaging information at a certain scattering angle from the object.

11. The apparatus according to claim 9 wherein the shape of the acoustically opaque member is selected to achieve a selected blocking pattern and passing pattern of the acoustic waves.

12. The apparatus according to claim 11 wherein the shape is selected to have sharp edges at at least one portion adjacent where the acoustic wave passes through.

13. The apparatus according to claim 11 wherein the acoustically opaque member is shaped to have a rounded surface adjacent to the location of the acoustic wave passing through.

14. The apparatus according to claim 11 wherein the acoustically opaque member is shaped to have a flat surface adjacent to the location of the acoustic wave passing through.

15. The apparatus according to claim 9 wherein the location of the acoustic blocking member is selected to be spaced from the lens by a distance based on the shape of the wave emanating from the acoustic transducer prior to the object.

16. The apparatus according to claim 9 wherein the imaging system is a holographic imaging system and creates an acoustical holographic image from a plurality of acoustic sound waves.

* * * * *